(12) United States Patent
Barrows

(10) Patent No.: US 7,198,641 B2
(45) Date of Patent: Apr. 3, 2007

(54) SCAFFOLDS FOR TISSUE ENGINEERED HAIR

(75) Inventor: Thomas H. Barrows, Austell, GA (US)

(73) Assignee: Aderans Research Institute, Inc., Beverly Hills, CA (US)

( * ) Notice: Subject to any disclaimer, the term of this patent is extended or adjusted under 35 U.S.C. 154(b) by 0 days.

(21) Appl. No.: 10/344,185

(22) PCT Filed: Aug. 7, 2001

(86) PCT No.: PCT/US01/24671

§ 371 (c)(1),
(2), (4) Date: Jul. 14, 2003

(87) PCT Pub. No.: WO02/15952

PCT Pub. Date: Feb. 28, 2002

(65) Prior Publication Data

US 2004/0054410 A1 Mar. 18, 2004

Related U.S. Application Data

(60) Provisional application No. 60/223,636, filed on Aug. 8, 2000.

(51) Int. Cl.
*A61F 2/10* (2006.01)
(52) U.S. Cl. .................................. 623/15.11
(58) Field of Classification Search .. 623/15.11–15.12; 264/28; 435/395, 371; 424/426; 606/132–133, 606/187
See application file for complete search history.

(56) References Cited

U.S. PATENT DOCUMENTS

| | | | |
|---|---|---|---|
| 2,946,769 A | 7/1960 | Rose et al. | |
| 3,025,323 A | 3/1962 | Rose et al. | |
| 3,596,292 A | * 8/1971 | Erb et al. | ............. 623/15.11 |
| 3,966,766 A | 6/1976 | Lehn | |
| 4,052,988 A | 10/1977 | Doddi et al. | |
| 4,104,195 A | 8/1978 | Ley et al. | |
| 4,209,607 A | 6/1980 | Shalaby et al. | |
| 4,226,243 A | 10/1980 | Shalaby et al. | |
| 4,242,931 A | 1/1981 | Clement | |
| 4,343,931 A | 8/1982 | Barrows | |
| 4,384,061 A | 5/1983 | Reiter et al. | |
| 4,429,080 A | 1/1984 | Casey et al. | |
| 4,458,678 A | 7/1984 | Yannas et al. | |
| 4,505,266 A | 3/1985 | Yannas et al. | |

(Continued)

FOREIGN PATENT DOCUMENTS

CA 2140090 8/1995

(Continued)

OTHER PUBLICATIONS

Atlas of Anatomy Barron's Educational Series, Inc. 1997, p. 72.*

(Continued)

*Primary Examiner*—Suzette Gherbi
(74) *Attorney, Agent, or Firm*—Michael Best & Friedrich LLP

(57) ABSTRACT

Porous, bioabsorbable scaffolds for tissue engineering of human hair follicles, methods for their manufacture and methods of their use in creating new hair.

12 Claims, 3 Drawing Sheets

U.S. PATENT DOCUMENTS

Figure 1:
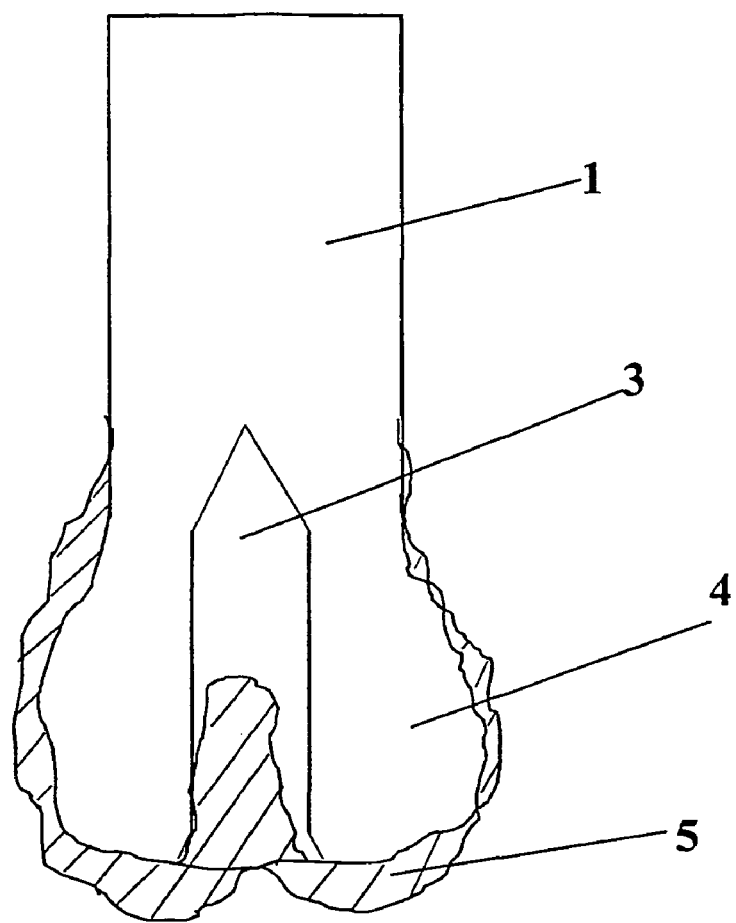

| | | |
|---|---|---|
| 4,529,792 A | 7/1985 | Barrows |
| 4,604,097 A | 8/1986 | Graves, Jr. et al. |
| 4,643,734 A | 2/1987 | Lin |
| 4,719,917 A | 1/1988 | Barrows et al. |
| 4,851,521 A | 7/1989 | della Valle et al. |
| 4,919,664 A | 4/1990 | Oliver et al. |
| 5,061,284 A * | 10/1991 | Laghi .................. 623/15.11 |
| 5,091,173 A | 2/1992 | Buultjens et al. |
| 5,133,739 A | 7/1992 | Bezwada et al. |
| 5,141,522 A | 8/1992 | Landi |
| 5,147,400 A | 9/1992 | Kaplan et al. |
| 5,194,473 A * | 3/1993 | Shinoda et al. ............. 524/263 |
| 5,198,507 A | 3/1993 | Kohn et al. |
| 5,286,837 A | 2/1994 | Barrows et al. |
| 5,393,323 A | 2/1995 | Simmons |
| 5,403,347 A | 4/1995 | Roby et al. |
| 5,415,378 A | 5/1995 | Craven |
| 5,423,778 A | 6/1995 | Eriksson et al. |
| 5,486,593 A | 1/1996 | Tang et al. |
| 5,502,092 A | 3/1996 | Suszko et al. |
| 5,514,378 A | 5/1996 | Cima et al. |
| 5,522,841 A | 6/1996 | Roby et al. |
| 5,545,208 A | 8/1996 | Wolff et al. |
| 5,556,783 A | 9/1996 | Lavker et al. |
| 5,578,046 A | 11/1996 | Liu et al. |
| 5,599,552 A | 2/1997 | Dunn et al. |
| 5,611,811 A | 3/1997 | Goldberg |
| 5,639,645 A | 6/1997 | Murata |
| 5,661,132 A | 8/1997 | Eriksson et al. |
| 5,667,961 A | 9/1997 | Bernard et al. |
| 5,674,286 A | 10/1997 | D'Alessio et al. |
| 5,677,355 A | 10/1997 | Shalaby et al. |
| 5,690,961 A | 11/1997 | Nguyen |
| 5,697,901 A | 12/1997 | Eriksson |
| 5,697,976 A | 12/1997 | Chesterfield et al. |
| 5,721,049 A | 2/1998 | Marcolongo et al. |
| 5,723,508 A | 3/1998 | Healy et al. |
| 5,756,094 A | 5/1998 | Lavker et al. |
| 5,770,417 A | 6/1998 | Vacanti et al. |
| 5,847,012 A | 12/1998 | Shalaby et al. |
| 5,898,040 A | 4/1999 | Shalaby et al. |
| 5,919,893 A | 7/1999 | Roby et al. |
| 5,939,323 A * | 8/1999 | Valentini et al. ............. 435/395 |
| 5,945,115 A | 8/1999 | Dunn et al. |
| 5,993,374 A | 11/1999 | Kick |
| 5,997,468 A | 12/1999 | Wolff et al. |
| 5,997,568 A | 12/1999 | Liu |
| 6,001,378 A | 12/1999 | Desjonqueres |
| 6,027,744 A | 2/2000 | Vacanti et al. |
| 6,031,148 A | 2/2000 | Hayes et al. |
| 6,051,750 A | 4/2000 | Bell |
| 6,093,200 A | 7/2000 | Liu et al. |
| 6,120,788 A | 9/2000 | Barrows |
| 6,147,135 A | 11/2000 | Yuan et al. |
| 6,159,950 A | 12/2000 | Crystal et al. |
| 6,303,697 B1 | 10/2001 | Yuan et al. |
| 6,333,029 B1 | 12/2001 | Vyakarnam et al. |
| 6,350,284 B1 | 2/2002 | Tormala et al. |
| 6,365,172 B1 | 4/2002 | Barrows |
| 6,383,220 B1 * | 5/2002 | van Blitterswijk et al. ....... 623/15.12 |
| 6,423,252 B1 * | 7/2002 | Chun et al. .................... 264/28 |
| 6,436,424 B1 | 8/2002 | Vogel et al. |
| 6,474,344 B2 * | 11/2002 | Yamada .................. 132/201 |
| 6,503,539 B2 | 1/2003 | Gestrelius et al. |
| 6,511,748 B1 | 1/2003 | Barrows |
| 6,569,143 B2 | 5/2003 | Alchas et al. |
| 6,613,798 B1 | 9/2003 | Porter et al. |
| 6,639,051 B2 | 10/2003 | Wang |
| 6,660,301 B1 | 12/2003 | Vogel et al. |
| 6,699,287 B2 * | 3/2004 | Son et al. ................. 623/15.12 |
| 6,773,713 B2 | 8/2004 | Bonassar et al. |
| 6,884,427 B1 | 4/2005 | Barrows |
| 2002/0049426 A1 | 4/2002 | Butler et al. |
| 2002/0083216 A1 | 6/2002 | Hickson et al. |
| 2002/0193740 A1 | 12/2002 | Alachas et al. |
| 2002/0193778 A1 | 12/2002 | Alachas et al. |
| 2002/0197326 A1 | 12/2002 | Vogel et al. |
| 2003/0009113 A1 | 1/2003 | Olson |
| 2003/0072784 A1* | 4/2003 | Williams .................... 424/426 |
| 2003/0077311 A1* | 4/2003 | Vyakarnam et al. ........ 424/426 |
| 2003/0161815 A1 | 8/2003 | Wolowacz et al. |
| 2003/0195625 A1* | 10/2003 | Castro et al. ............ 623/15.11 |
| 2003/0203003 A1* | 10/2003 | Nelson et al. .............. 424/426 |
| 2003/0208138 A1 | 11/2003 | Olson |
| 2003/0211083 A1 | 11/2003 | Vogel et al. |
| 2004/0033598 A1* | 2/2004 | Vacanti et al. .............. 435/371 |
| 2004/0039438 A1 | 2/2004 | Alt |
| 2004/0054410 A1 | 3/2004 | Barrows |
| 2004/0057937 A1 | 3/2004 | Jahoda et al. |
| 2004/0068284 A1 | 4/2004 | Barrows |
| 2004/0096514 A1 | 5/2004 | Vogel |

FOREIGN PATENT DOCUMENTS

| | | |
|---|---|---|
| CA | 2199918 | 9/1997 |
| EP | 0236014 | 9/1987 |
| EP | 405656 | 1/1991 |
| EP | 1002859 A | 5/2000 |
| EP | 971679 | 6/2002 |
| EP | 00845963 | 9/2003 |
| EP | 1083874 | 1/2004 |
| EP | 1089704 | 2/2004 |
| EP | 1098626 | 5/2004 |
| EP | 1437042 | 7/2004 |
| JP | 3273028 | 12/1991 |
| JP | 4-108444 | 4/1992 |
| JP | 7-48769 | 2/1995 |
| JP | 10-136977 | 5/1998 |
| JP | 2003328229 | 11/2003 |
| WO | WO199962491 | 6/1998 |
| WO | WO 9844027 A | 10/1998 |
| WO | WO199847471 | 10/1998 |
| WO | WO 9934750 A | 7/1999 |
| WO | WO200003749 | 7/1999 |
| WO | WO 0029553 A | 5/2000 |
| WO | WO 0045736 A | 8/2000 |
| WO | WO 0062829 A | 10/2000 |
| WO | WO200158413 | 8/2001 |
| WO | WO200166472 | 9/2001 |
| WO | WO200170132 | 9/2001 |
| WO | WO200170289 | 9/2001 |
| WO | WO200170290 | 9/2001 |
| WO | WO200170291 | 9/2001 |
| WO | WO2002060396 | 8/2002 |
| WO | WO2002070728 | 9/2002 |
| WO | WO2003022043 | 3/2003 |
| WO | WO 03/104443 A2 * | 12/2003 |
| WO | WO2004044188 | 5/2004 |

OTHER PUBLICATIONS

U.S. Appl. No. 10/810,518, filed Mar. 2004, Barrows.
U.S. Appl. No. 11/107,230, filed Apr. 2005, Barrows.
U.S. Appl. No. 11/203,804, filed Aug. 2005, Barrows.
Arase, S. et al., "Co-culture of human hair follicles and dermal papillae in a collagen matrix," J. Dermatol. (1990) 17:667-676.
Arase, Seigi, et al., "Culture of dispersed hair follicle cells from plucked out hairs without a feeder layer," Tokushima J. exp. Med. (1989) 36:87-95.
Arias, AM and Stewart A. (2002) Molecular Principles of Animal Development Oxford University Press, Oxford [Book—Not Included].
Atala A, & Lanza RP, eds (2002). Methods of Tissue Engineering, Academic Press, NY [Book—Not Included].

Atala A. (2004) Tissue engineering and regenerative medicine: concepts for clinical application. Rejuvenation Res 7:15-31.
Barrows TH, Cochran SA, Griffin EI and Solomon AR, "Tissue Engineered Human Hair: Preliminary Clinical Results" TE2002: International Workshop on Tissue Engineering, St. Gallen, Switzerland (Feb. 2002).
Bieberich et al., "Differential expresion of the Hox 3.1 gene in adult mouse skin" Ann NY Acad Sci (1991) 642:346-354.
Bioglass, http://www.usbiomat.com/bioglass.html Dec. 28, 2000.
Chang et al. (2004) "Sculpting skin appendages out of epidermal layers via temporarally and spatially regulated apoptotic events" J Invest Dermatol 122:1348-1355.
Chase, H.B. et al., "Changes in the skin in relation to the hair growth cycle" The Anatomical Record, The Wistar Institute of Anatomy and Biology, Philadelphia, PA (1953) 116:75-81.
Chiang et al., 1999, "Essential Role for Sonic hedgehog during Hair Folllicle Morphogenesis" Dev. Biol. 205:1-9.
Clark et al., 1988, Mol. Cell. Biol. Of Wound Repair, Plenum Pub., Co. New York [Book—Not Included].
Cohen J, The transplantation of individual rat and guinea-pig whisker papillae. J Embryol Exp Morphol. Mar. 1961;9:117-27.
Cotsarelis G, Sun TT, Lavker RM. (1990) Label-retaining cells reside in the bulge area of pilosebaceous unit. Implications for follicular stem cells, hair cycle and skin carcinogenesis Cell 61:1329-1337.
Coulombe, P.A. and Omary, M.B., "Hard and soft principles defingn the structure, function and regulation of keratin intermediate filaments" Curr Opin Cell Biol (2002) 14:110-122.
Deleens, G., et al., SPIE 39th Ann. Tech. Conf., Boston, MA May 4-7, 1981.
Dlugosz, (1999), "The Hedgehog and the hair follicle: a growing relationship", The Journal of Clinical Investigation, vol. 104, 851-853.
Domashenko, et al., (2000), "Efficient delivery of transgenes to human hair follicle progenitor cells using topical lipoplex", Nature Biotechnology, vol. 18, 420-423.
Dry, F.W., "The coat of the mouse (*Mus musculus*)," J. Genetics, Bateson and Punnett eds., (1926) 287-340.
Du Cros et al. (1995) Association of versican with dermal matricies and its potential role in hair follicle development and cycling: J Invest Dermatol 105:426-31.
Dyce et al., (2004) "Stem cells with multilineage potential derived from porcine skin" Bioche Biophys Res Commun, 316:651-658.
Ebling FJ, "The biology of hair" Dermatol Clin Jul. 1987;5(3):467-81.
Elsdale T, Bard J, (1972) "Cellular Interactions in Mass Cultures of Human Diploid Fibroblasts" Nature 236: 152-155.
Evans, G.R. et al., "In vivo evaluation of poly(L-lacatic acid) porous conduits for peripheral nerve regeneration," Biomaterials (1999) 20:1109-1115.
Favier B, et al. "Localisation of members of the notch system and the differentiation of vibrissa hair follicles: receptors, ligands, and fring modulators" Dev Dyn Jul. 2000;218(3):426-37.
Ferraris et al., 1997,"Adult epidermal keratinocytes are endowed with pilosebaceous forming abilities" Int. J. Dev. Biol., 41:491-498.
Fieser, L.F. and Fieser, M., "Reagents for Organic Synthesis," John Wiley and Sons, Inc. (1967) 704-706.
Foitzik, et al., (2000) "Control of murine hair follicle regression (catagen) by TGF-B1 in vitro", Catagen Induction by TGF-B1, The FASEB Journal, vol. 14, 752-760.
Fujie et al. (2001) "The chemotactic effect of a dermal papilla cell-derived factor on outer root sheath cells," J. Dermatol. Sci. 25(3):206-12.
Gambardella et al., (2000) "Pattern of Expression of the Transcription Factor Krox-20 in mouse hair follicle", Mech. Of Dev. 96:215-218.
Gharzi et al., "Plasticity of hair follicle dermal cells in wound healing and induction," Exp. Dermat. (2003) 12:126-136.
Gilbert, S.F., "Development of the tetrapod limb," Developmental Biology, Sinauer Associates, Inc. (2000) 503-521.
Gurdon, J.B. "The localization of an inductive response" Development (1989) 105:27-33.

Hage JJ and Freerk GB, "Surgical Depilation for the Treatment of Pseudofolliculitis or Local Hirsutism of the Face: Experience in the First 40 Patients" Surgical Depilation for Pseudofolliculits (1991) 88(3):446-451.
Handjiski, B.K. et al., "Alkaline phosphatase activity and localizatoin during the murine hair cycle" Br J Dermatol (1994) 131:303-310.
Hansen, L.S. et al., "The influence of the hair cycle on the thickness of mouse skin" Anat Rec (1984) 210:569-573.
Hardy M, "The development of mouse hair in vitro wit some observations on pigmentation" J. Anat (1949) 83:364-384.
Hardy, M., "The secret life of the hair follicle," Trends in Genetics (1992) 8:55-61.
Hashimoto et al., "Histological examination of human hair follicles grafted onto severe combined immunodeficient (SCID) mice," Hair Research for the Next Millenium eds., DJJ Van Neste and VA Randall, Elsevier Science BV, Amsterdam (1996) 141-145.
Haynesworth, et al., (1993) "Diminution of the Number of Mesenchymal Stem Cells as a Cause for Skeletal Aging" Chapter 7, 79-87.(Eds. J.A. Buckwater & V.M. Goldberg).
Horne et al., (1992) Development 116(3):563-571, abstract.
Horne, Kenneth A, et al. "Whisker growth induced by implantation of cultured vibrissa dermal papilla cells in the adult rat" J Embryol Exp Morphol. Sep. 1986;97:111-24.
Hu M, Sabelmann EE, Lai S, Timek EK, Zhang F, Hentz, VR and Lineaweaver, CW, Journal of Biomedical Materials Research, vol. 47, pp. 79-84 (1999).
Inaba (1992) "Chapter 16. The Question of Hair Regeneration, In: Human Body Odor, Etiology Treatment and Related Factors" Springer-Verlag, Tokyo (printed in Hong Kong) 235-260.
Inamatsu et al., "Establishment of rat dermal papilla cell lines that sustain the potency to induce hair follicles from afollicular skin" J Invest Dermatol. Nov. 1998;111(5):767-75.
Jahoda and Oliver, "The growth of vibrissa dermal papilla cells in vitro," Br. J. Dermatol. (1981) 105:623-627.
Jahoda and Reynolds (2001) "Hair follicle dermal sheath cells: unsung participants in wound healing" Lancet 358:1445-1448.
Jahoda CA, "Induction of follicle formation and hair growth by vibrissa dermal papillae implanted into rat ear wounds: vibrissa-type fibres are specified" Development. Aug. 1992;115(4):1103-9.
Jahoda Cab, et al. (1993) "Induction of Hair Growth in Ear Wounds by Cultured Dermal Papilla Cells" J Invest Dermatol 101(4):584-590.
Jahoda Cab, et al., (1996) "Human Hair follicle regeneration following amputation and grafting into the nude mouse" J Invest Dermatol, 107(6):804-807.
Jahoda Cab, et al., "Induction of hair growth by implantation of cultured dermal papilla cells" Nature. Oct. 11-17 1984;311(5986):560-2.
Jahoda, C.A.B. et al., "Hair follicle dermal cells differentiate into adipogenic and osteogenic lineages," Exp. Dermatol. (2003) 12:849-859.
Jahoda et al. "Dermal-Epidermal Interactions, Adult Follicle-Derived Cell Populations and Hair Growth" Dermatologic Clinics W. B. Saunders Co. London G.B., Oct. 1996, 14(4):573-583; XP002913549.
Jahoda, Cab, et al., "Dermal-epidermal interactions—follicle-derived cell populations in the study of hair-growth mechanisms," Journal of Investigative Dermatology (1993) 101(1):33S-38S.
Jahoda, et al., "Trans-species hair growth induction by human hair follicle dermal papillae," Exp. Dermatol. (2001) 10:229-237.
Kamimura, et al., "Primary mouse keratinocyte cultures contain hair follicle progenitor cells with multiple differentiation potential," Journal of Investigative Dermatology (1997) 109(4):534-540.
Kanzler, B. et al., "Differential expression of two different homeobox gene families during mouse tegument morphogenesis," Int. J. Dev. Biol. (1994) 38:633-640.
Katayama, S. et al., "Synthesis of Alternating Polyamide Esters by Melt and Solution Polycondensations of N,N'-Di(6-hydroxycaproyl) dimines and N-6-Hydroxycaproyl Aminoalcohol with Terephthalic and Adipic Dimethyl Esters and Dichlorides" J. of Applied Polymer Science (1976) 20:975-994.

Kaufman, C.K. et al., "GATA-3: an unexpected regulator of cell lineage determination in skin," Gene Dev (2003) 17:2108-2122.

Kemp CB, et al., (1973) "Effect of Transplantation Site on the Results of Pancreatic Islet Isografts in Diabetic Rats" Diabetologia 9:486-491.

Kishimoto et al., "Selective activation of the versican promoter by epithelial- mesenchymal interactions during hair follicle development" Proc Natl Acad Sci U S A. Jun. 22 1999;96(13):7336-41.

Kishimoto, et al., "Wnt signaling maintains the hair-inducing activity of the dermal papilla" Genes Dev. May 15, 2000;14(10):1181-5.

Lako et al., (2002) Hair follicle dermal clls repopulate the mouse haematopoietic system: J. Cell Sci 115:3967-3974.

Lavker, RM, et al., Hair follicle stem cells: Their location, role in hair cycle, and involvement in skin tumor formation, Journal of Investigative Dermatology (1993) 101(1):16S-26S.

Lanford PJ, et al. "Notch signalling pathway mediates hair cell development in mammalian cochlea," Nat. Genet (1999) 21(3):289-292.

Lewis AK, et al. "Distinct expression patterns of notch family receptors and ligands during development of the mammalian inner ear" Mech Dev Nov. 1998:78(1):159-163.

Lichti et al., "In vivo regulation of murine hair growth: insights from grafting defined cell populations onto nude mice" J Invest Dermatol. Jul. 1993;101(1 Suppl):124S-129S.

Lichti, AB, et al., "Hair follicle development and hair growth from defined cell populations granted onto nude mice," J Invest Dermat (1995) 104(5):43S-44S.

Lin et al., "Activation of the notch pathway in the hair cortex leads to aberrant differentiation of the adjacent hair-shaft layers," Development (2000) 127:2421-2432.

Luo Y., et al. "Modification of Natural Polymers: Hyaluronic Acid," Methods of Tissue Engineering, Chapter 45, A. Atala and RP Lanza. eds., Academic Press (2002) 539-553.

Ma, L. et al., "Cyclic alopecia in Msx2 mutants: defects in hair cycling and hair shaft differentiation" Development (2003) 130:379-389.

Ma, Peter X., Ruiyun Zhang, "Synthetic nano-scale fibrous extracellular matrix" J. Biomed. Materials Res. 46(1):60-72 (Jul. 1999) Abstract.

Malkinson F and Keane JT, (1978) "Hair Matrix Cell Kinettics; A Selective Review" Int'l J Dermatol, 17(7):536-551.

Matsuzaki et al., Differentiation, 60(5):287-297 abstract.

McElwee et al., "Cultured Peribulbar Dermal Sheath Cells Can Induce Hair Follicle Development and Contribute to the Dermal Sheath and Dermal Papilla" 2003 J. Invest Dermatol 121:1267-1275.

Messenger AG, "The control of hair growth: an overview" J Invest Dermatol Jul. 1993;101(1 Suppl):4S-9S.

Messenger, "Hair Follicle Tissue Culture" Br. J. Dermatol. (1985) 113:639-640.

Messenger, "The culture of dermal papilla cells from human hair follicles," British Journal of Dermatology (1984) 110:685-689.

Michalopoulos G. and Pitot HE, (1975) "Primary Culture of Parenchymal Liver Cells on Collagen Membranes" Experimental Cell Research 94:70-78.

Mills, A.A. et al., "p63 is a p53 homologue required for limb and epidermal morphogenesis," Nature (1999) 398:708-713.

Morris RJ, Liu Y, Marles L, Yang Z, Trempus C, Li S, Lin JS, Sawicki JA, & Cotsarelis G. (2004) Capturing and profiling adult hair follicle stem cells. Nature Biotechnology 22:1-7.

Moscona, A., "Rotation-mediated histogenetic aggregation of dissociated cells. A quantifiable approach to cell interactions in vitro," Exp. Cell Research (1961) 22:455-475.

Nichols et al., "Formation of pluripotent stem cells in the mammalian embryo depends onthe POU transcription factor" Cell (1998) 95:379-391.

Nixon et al., 1996, "Transforming Growth factor-alpha Immunoreactivity During Induced Hair Follicle Growth Cycles in Sheep and Ferrets" J. Histochem. Cytochem, 44:377-387.

Oliver RF (1980) "Local interactions in mammalian hair growth" Mammalian Hair Growth, 199-210.

Oliver RF and Jahoda Cab, (1989) "The Dermal Papilla and Maintenance of Hair Growth" Dermal Papilla and Hair Growth Chapter 4, 51-67. Cambridge: Cambridge University Press.

Oliver RF, (1971) "The dermal papilla and the development of hair growth" J Soc Cosmet Chem 22:741-755.

Oliver RF, "Whisker growth after removal of the dermal papilla and lengths of follicle in the hooded rat" J Embryol Exp Morphol. Jun. 1966;15(3):331-47.

Oliver RF, "Histological studies of whisker regeneration in the hooded rat." J Embryol Exp Morphol. Oct. 1966;16(2):231-44.

Oliver RF, "The experimental induction of whisker growth in the hooded rat by implantation of dermal papillae" .J Embryol Exp Morphol. Aug. 1967;18(1):43-51.

Oliver RF, "The induction of hair follicle formation in the adult hooded rat by vibrissa dermal papillae" J Embryol Exp Morphol. Feb. 1970;23(1):219-36.

Oshima et al., (2001) "Morphogenesis and renewal of hair follicles from adult multipotent stem cells" Cell, 104:233-245.

Patrick, C.W., et al., eds., "Prospectus of Tissue Engineering," Frontiers in Tissue Engineering, Elsiver Science, Inc., New York, (1998) 3-11.

Paus, R. et al., "Telogen skin contains an inhibitor of hair growth," Brit J Dermatol (1990) 122:777-784.

Paus et al., "A comprehensive guide for the recognition and classification of distinct stages of hair follicle morphogenesis" J Invest Dermatol (1999) 113:523-532.

Philpott et al., 1994, "Effects of Insulin and Insulin-Like Growth Factors on Cultured Human Hair Folicles: IGF-I at Physiologic Concentrations Is an Important Regulator of Hair Follicle Growth In Vitro" J. Invest. Derm., 120:857-861.

Philpott, M. et al., "In vitro maintenance of isolated hair follicles: current status and future development," Ex. Dermatol. (1999) 8(4):317-319 Abstract.

Pisansarakit, P. et al. Arch Dermatol Res. 183(5):321-327 abstract. (Listed previously as CSIRO et al.).

Pispa, J. and Thesleff, I., "Mechanisms of ectodermal organogenesis," Dev Biol (2003) 262:195-205.

Powell, B.C. et al., "The Notch Signalling pathway in hair growth" Mech Dev (1998) 78:189-192.

Prouty, S.M. et al., "Fibroblast-dependent induction of a murine skin lesion similar to human nevus sebaceus of jadassohn," Lab. Invest (1997) 6(2):179-189.

Prouty, S.M. et al., "Fibroblast-dependent induction of a murine skin lesion with similarity to human common blue nevus" Am J Pathol. (1996) 148(6):1871-1885.

Raposio, E. et al., "Follicular bisection in hair transplantation surgery: an in vitro model," Plastic and Reconstructive Surgery (1998) 221-226.

Reginelli et al. (1995) "Digit tip regeneration correlates with regions of Msx1 (Hox 7) expression in fetal and newborn mice" Development 121:1065-1076.

Remmler D, et al., "Use of injectable cultured human fibroblasts for percutaneous tissue implantation," Arch Otolaryngol Head Neck Surg (1989) 115:837-844.

Reynolds and Jahoda,"Cultured dermal papilla cells induce follicle formation and hair growth by transdifferentiation of an adult epidermis" Development (1992) 115:587-593.

Reynolds AJ and Jahoda Cab, (1991a) "Inductive Properties of Hair Follicle Cells" Annals New York Academy of Sciences, 624:226-242.

Reynolds AJ, et al. (1992) "Human Hair Follical Germinative Epidermal Cell Culture" J Invest Dermatol, 101(4): 634-638.

Reynolds AJ, Jahoda, CA, "Hair follicle reconstructive in vitro" J. Dermatol Sci Jul. 1994;7 Suppl:S84-97.

Reynolds AJ and Jahoda, CA, "Hair fibre progenitor: developmental status and interactive potential" Dev Biol (1993) 4:241-250.

Rogers et al. "Cultivation of murine hair follicles as organoids in a collagen matrix" J Invest Dermatol. Oct. 1987;89(4):369-79.

Sambrook et al., 1989, Molecular Cloning: A Laboratory Manual, Cold Spring Harbor Laboratory, New York [Book—Not Included].

Sato, et al., "Induction of the hair growth phase in postnatal mice by localized transient expression of sonic hedgehog", J. Clin. Invest. (1999) 104:855-864.

Scholer, H.R. et al., "A family of octmer-specific proteins present during mouse embryogenesis: evidence for germline-specific expression of an Oct factor," EMBO J (1989) 8(9):2543-2550.

Schwarz, M.A. et al., "Epithelial-mesenchymal interactions are linked to neovacsularization" Amer J Respir Cell Mol Biol (2004) 30:784-792.

Scott DM, et al. (1995) "Identification of a mouse male-specific transplantation antigen, H-Y" Nature 376:695-698.

Stenn and Paus, "Controls of Hair Follicle Cycling" Physiological Reviews (2001) 81(1):449-494. [Cited As 2002 In Specification].

Stenn et al., "Re-epithelialization," Chapter 14 in: The Molecular and Cellular Biology of Wound Repair, Eds, RAF Clark, Plenum Press (1988) 321-335.

Stenn KS, "Induction of hair follicle growth" J. Invest Dermatol (1991) 96(5):80S.

Stenn, et al., "Hair follicle growth controls," Dermatol Clinics (1996) 14:543-558.

Stenn, K. et al., "Growth of the Hair Follicle: A Cycling and Regenerating Biological System," The Molecular Basis of Epithelial Appendage Morphogenesis, ed. C-M Chuong, Landes Publ. Austin TX (1998) 111-130.

Sundberg et al. (2000) "Asebia-2J(Scd1(ab2J)): a new allele and a model for scarring alopecia" Amer J Path 156:2067-2075.

Takeda, A. et al., "Histodifferentiation of hair follicles in grafting of cell aggregates obtained by rotation culture of embryonic rat skin" Scand J. Plas Reconstr Hand Surg (1998) 32:359-364.

Takeda, A. et al., "Reconstitution of hair follicles by rotation culture," Hair Research for the Next Millennium, eds. Van Neste and Randall, Elsevier Science BV (1996) 191-193.

Taylor et al., "Involvement of follicular stem cells in forming not only the follicle but also the epidermis" Cell (2000) 102:451-461.

Tomihata K and Ikada Y, "Crosslinking of hyaluronic acid with water-soluble carbodiimide" J. Biomed. Mater. Res. (1997) 37:243-251.

Trempus et al. "Enrichment for living murine keratinocytes from the hair follicle bulge with the cell surface marker CD34" J Invest Dermatol (2003) 120:501-511.

Tsonis, P.A. Limb Regeneration, Cambridge University Press, Cambridge (1996) 241 (Book—Not Included).

Watson Saj, et al., (1994) "Sheep vibrissa papillae induce hair follicle formation in heterotypic skin equivalents" Br J Dermatol, 131:827-835.

Weinberg, et al. Reconstruction of hair follicle development in vivo: determination of follicle formation, hair growth, and hair quality by dermal cells: Journal of Investigative Dermatology 100(3), Mar. 1993, 229-235.

Widelitz, R.B. and Chuong, C-M., "Early events in skin appendage formation: Induction of epithelial placodes and condensation of dermal mesenchyme," J Invest Dermatol Sympos Proc (1999) 4(3):302-306.

Widelitz et al., "Molecular Histology in Skin Appendage Morphogenesis" Microsc. Res. Tech. (1997) 38:452-465.

Williams, D. et al., "Isolation and culture of follicular papillae from murine vibrissae: an introductory approach," Br. J. Dermatol. (1994) 130:290-297.

Wilson C. et al., "Cells withing the bulge region of moust hair follicle transiently proliferate during early anagen: heterogeneity and funtional differences of various hair cycles" Differentiation (1994) 55(2):127-36.

Xing, L and Kobayashi, K., "Ability of Transplanted Cultured Epithelium to Respond to Dermal Papillae," Tissue Engineering (2001) 7:535-544.

Yagita, "CD95 ligand graft rejection" Nature (1996) 379:682-683.

Yang et al. "p63 is essential for regenerative proliferation in limb, craniofacial and epithelial development" Nature (1999) 398:714-718.

Yang, et al., "Upper-Human Hair Follicle Contains a Subpopulation of Keratinocytes with Superior In Vitro Proliferative Potential", In vitro Growth of Follicular Keratinocytes, The Journal of Investigative Dermatology, (1993) 101(5):652-659.

Yuspa SH, et al., "Regulation of hair follicle development: An in vitro model for hair follicle invasion of dermis and associated connective tissue remodeling," J Invest Derm (1993) 101(1):27S-32S.

Stenn, K.S. et al., "Bioengineering the hair follicle: fringe benefits of stem cell technology," Curr. Opin. Biotech. (2005) 16(5):493-497.

Worst, P.K.M. et al., "Reformation of organized epidermal structure by transplantation of suspensions and cultures of epidermal and dermal cells," Cell Tiss. Res. (1982) 225(1):65-77.

Zheng, Y. et al., "Organogenesis from dissociated cells: generation of mature cycling hair follicles from skin-derived cells," J. Invest. Dermatol. (2005) 124:867-876.

Nam, Y.S. and Park, T.G., "Porous biodegradable polymeric scaffolds prepared by thermally induced phase separation" *The Journal of Biomedical Materials Research*, Oct. 1999, vol. 47, No. 1, 8-17.

Reynolds, A.M. et al., "Trans-gender induction of hair follicles" *Nature*, 402, 33-34 Nov. 4, 1999.

* cited by examiner

SCAFFOLDS FOR TISSUE ENGINEERED HAIR

This application claims priority to PCT/US01/24671 filed Aug. 7, 2001, which claims priority to U.S. Provisional Patent Application No. 60/223,636 filed Aug. 8, 2000, all of which are incorporated herein by reference.

BACKGROUND OF THE INVENTION

Male pattern baldness is a common condition that is often treated by hair transplant surgery. In this procedure hair follicles from areas of the scalp that are not within the baldness pattern are excised and re-implanted to create the illusion of a fuller head of hair. In fact, no new hair is created by this procedure, which is limited by the number of follicles that can be harvested for re-distribution. Thus, there is a great need, satisfied by the present invention, for a means for stimulating the growth of multiple new hair follicles in the scalp of an individual.

BRIEF SUMMARY OF THE INVENTION

This invention relates to new bioabsorbable scaffolds that are useful for the tissue engineering of new hair follicles and to methods for their manufacture and to methods of their use in creating new hair. More specifically it relates to new and useful bioabsorbable porous structures that have the correct architecture to facilitate culturing of the appropriate follicle progenitor cells and their development into normal, functional, hair-producing follicles. The invention also relates to methods of making and using bioabsorbable scaffolds to implant and grow new hair follicles in vitro and in vivo.

BRIEF DESCRIPTION OF THE DRAWING(S)

FIG. 1 is a cross-sectional view of form 1, with porous polymer precursor 5 coating the distal end 4 of form 1.

Figure 2:
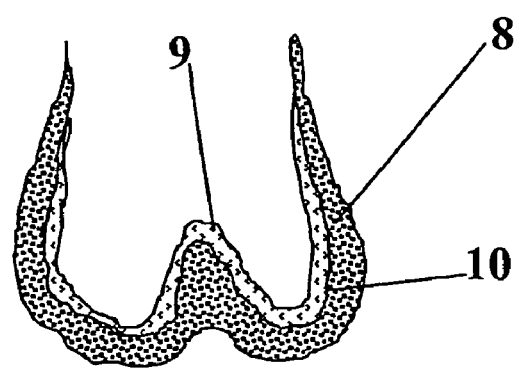

FIG. 2 is a cross-sectional view of porous scaffold 8 with a layer of follicle progenitor cells 9 lining the inner surface 10 of the porous scaffold.

Figure 3:
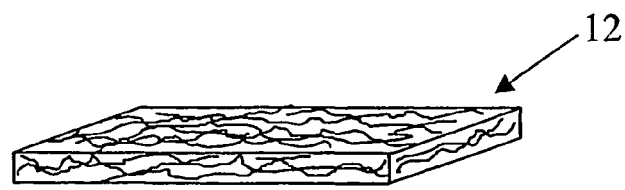

FIG. 3 is a side, three-dimensional view of a non-woven web 12 of bioabsorbable porous polymer material.

Figure 4:
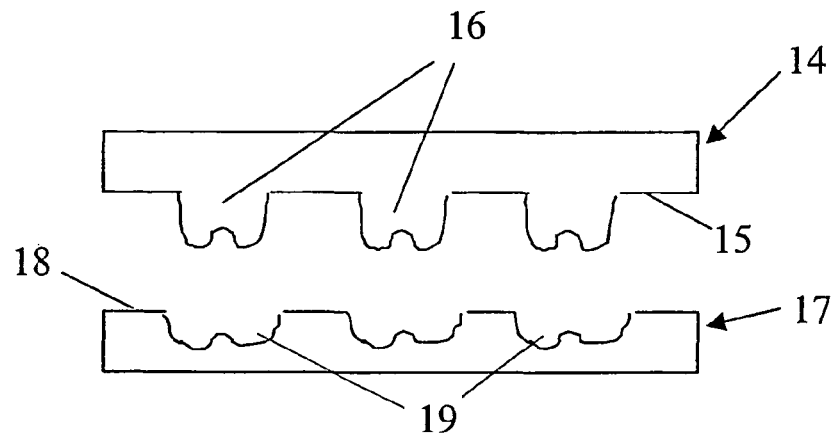

FIG. 4 is a cross-sectional side view of a mold for forming a porous scaffold, comprising a top plate 14 having a bottom side 15 with forms 16 protruding from the bottom side of the top plate, and a bottom plate 17 with a top side 18 defining wells 19 designed to receive the forms 16 of the top plate 14, when aligned therewith.

Figure 5:
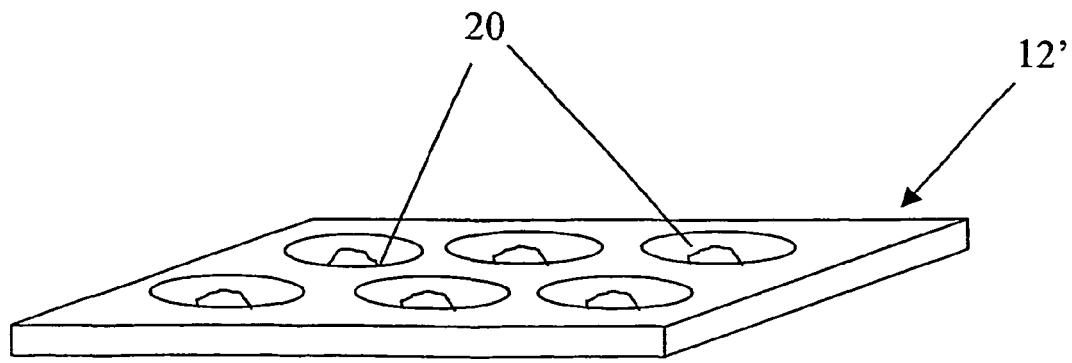

FIG. 5 is a top, slightly raised view of the non-woven web 12' after having been pressed and heated in the mold of FIG. 4, forming depressions 20 in the non-woven web.

Figure 6:
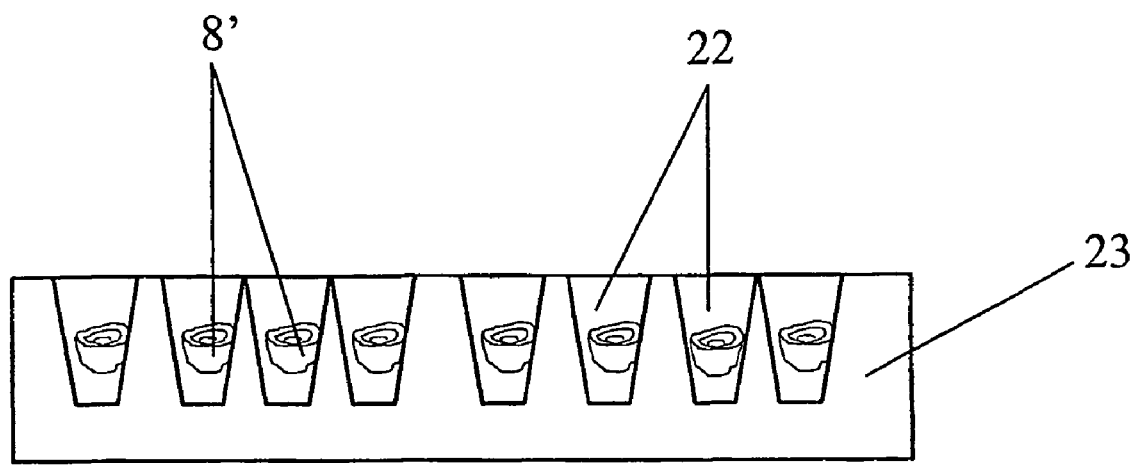

FIG. 6 is a cross-sectional view of a set of scaffolds 10', after transfer to wells 22 of a cell culture dish 23.

DETAILED DESCRIPTION OF THE INVENTION

In one aspect, the present invention comprises porous bioabsorbable scaffolds that are in the approximate shape of the normal hair follicle bulb, and designed to promote the formation of a hair follicle when seeded with hair follicle cells and implanted intradermally into a living host.

The scaffolds of the present invention are preferably comprised of a bioabsorbable polymer, selected from any of a wide variety of synthetic and natural polymers that are commonly used in clinical practice and in biomedical research. The scaffolds are more preferably comprised of a polymer selected from the group consisting of poly(lactic acid), poly(glycolic acid), poly(trimethylene carbonate), poly(amino acid)s, tyrosine-derived poly(carbonate)s, poly (carbonate)s, poly(caprolactone), poly(para-dioxanone), poly(ester)s, poly(ester-amide)s, poly(anhydride)s, poly (ortho ester)s, poly(amino acid)s, collagen, gelatin, serum albumin, proteins, carbohydrates, poly(ethylene glycol)s, poly(propylene glycol)s, poly(acrylate ester)s, poly(methacrylate ester)s, poly(vinyl alcohol), and copolymers, blends and mixtures of said polymers.

When the scaffold is comprised of a synthetic polymer, it is preferably a synthetic polymer formed from any one or combination of the following monomers: L-lactide, d,l-lactide, glycolide, trimethylene carbonate, caprolactone, and para-dioxanone. Other preferred synthetic polymers for use in making the scaffold of the present invention include poly(ethylene glycol), poly(vinyl alcohol), poly(acrylic acid) and other water soluble polymers that have been crosslinked with degradable linkages and any bioabsorbable hydrogel that has been modified to support cell attachment.

When the scaffold is comprised of a crosslinked or otherwise insoluble or insolubilized naturally occurring polymer, it is preferably a polymer selected from the group consisting of hyaluronic acid, human serum albumin, collagen, gelatin, cellulose derivatives, starch, dextrin, chitosan, and other proteins, glycoproteins, lipoproteins, polysaccharides, and biopolymers.

A preferred scaffold of the present invention has an inner surface which is preferably in the shape of the outer surface of a hair root or bulb. The inner surface of the scaffold is preferably porous. The porosity of the scaffold is preferably sufficient to enable hair follicle cells to be adsorbed by the inner surface of the scaffold when placed into contact therewith, e.g., in a cell culture solution.

Methods of making the porous bioabsorbable scaffolds of the present invention are disclosed herein, below. Such methods include procedures for creating porosity in bioabsorbable materials and procedures for molding, shaping, or sculpting said porous scaffolds into the desired configuration. The present invention is not limited to scaffolds produced according to the specific methods disclosed herein, below, as it is contemplated that the scaffolds could be made using variations of the disclosed methods, or by adapting known means used to manufacture porous polymers.

Any one of a number of different means are suitable for creating the porosity of the scaffolds of the present invention. A preferred method for creating porosity involves the use of "blowing agents". These are chemical additives that decompose at known temperatures with the liberation of gases that cause foaming in the molten polymer and porosity in the resultant cooled material. A number of useful blowing agents are commercially available under the trade name of Celogen™ (Uniroyal Chemical Co.). One example of a traditional blowing agent is azodicarbonamide. Another blowing agent that may be especially useful in the present invention due to its compatibility with bioabsorbable polymers is urea dicarboxylic acid anhydride, described in U.S. Pat. No. 4,104,195, the teachings of which are incorporated herein. The use of blowing agents can produce both open cell and closed cell foams. In the present invention open cells are desired and closed cells are to be avoided. Thus the conditions used in the manufacture of the porous coating are preferably optimized to achieve an open cell structure known as "reticulated" foam. The porosity of the scaffold is preferably due to interconnected pores in the size range of 0.1 to 1,000 microns, more preferably in the size range of 1 to 500 microns.

In an alternative embodiment, the porosity of the scaffold is due to the fact that the scaffold has a fibrous structure. When the scaffold has a fibrous structure, the fibers are preferably bonded together. The fibers of such a preferred structure are more preferably comprised of a core and sheath structure, said sheath being lower melting than said core, and bonded together by means of inter-fiber welds in the sheaths at points of contact.

One preferred method of making a scaffold of the present invention, (hereinafter, "the dissolution method") comprises the following steps:

1. Provide a bioabsorbable polymer that is soluble in a solvent (solvent A).
2. Provide a form in the shape of the desired scaffold made of a material that is soluble in a different solvent (solvent B) and that is substantially insoluble in solvent A.
3. Coat the form with particles of a pore-forming substance that is also soluble in solvent B or in a third solvent (solvent C).
4. Dissolve the bioabsorbable polymer in solvent A and apply the resultant solution to the particle-covered form.
5. Remove solvent A by evaporation or other suitable means.
6. Use solvent B to dissolve said form and said particles.
7. Remove solvent B from the finished porous scaffold.
8. If required, use solvent C additionally to remove said particles.

The dissolution method is illustrated in FIG. 1, which shows form 1 in cross-section with distal end 4 coated with porous polymer precursor 5, a mixture of particles of the pore forming substance and a solution of the polymer dissolved in solvent A. Note that the distal end 4 of form 1 is bulbous in shape, and includes a cavity 3 sufficiently large enough to enable some of the porous polymer precursor 5 to enter the cavity. Once a porous polymer has been formed from the porous polymer precursor 5 of FIG. 1, as described above, and the form has been dissolved, the resulting porous scaffold can be seeded with hair follicle progenitor cells and used as described below.

FIG. 2 is a cross-sectional view that shows the porous scaffold 8 obtained by dissolving and washing away the pore forming substance and form, as described above, leaving only the bioabsorbable polymer. The scaffold 8 is shown with follicle progenitor cells 9 seeded on to the inner surface 10 of the scaffold, having taken the shape of the scaffold. The structure shown in FIG. 2 could be directly implanted into the dermis to promote the growth of a new single hair fiber from the tissue engineered follicle. However, to better ensure that the transplanted engineered follicle matures, the structure shown in FIG. 2 is more preferably cultured with additional cells prior to implantation.

Examples of materials that can be used to create the form and solvents that can be selected for use as solvent B in the dissolution method, described above, include the following combinations: poly(ethylene oxide) and water; paraffin wax and hexane; and polystyrene and acetone. The pore forming substance and form material must be selected from those substances that have low solubility in solvent A, used to introduce the bioabsorbable polymer into the structure. These choices are further exemplified in Table 1 below where the following abbreviations have been used: PLGA is a copolymer of lactic and glycolic acids and PEO is poly (ethylene oxide).

TABLE 1

| Bioabsorbable polymer | Form material | Pore forming substance | Solvent A | Solvent B | Solvent C |
|---|---|---|---|---|---|
| PLGA | PEO | Sodium chloride | Acetone | Water | Water |
| PLGA | Wax | Glucose | Acetone | Hexane | Water |
| Collagen | Wax | Polystyrene | Water | Hexane | Acetone |

A modification of the dissolution method is exemplified by reversing the sequence of steps of creating the desired structure followed by seeding with progenitor cells. Thus a porous scaffold structure can first be formed in the shape of a disc, for example by adding a solution of polymer in an organic solvent to appropriately sized salt particles in a cylindrical container followed by evaporation of said solvent and removal of the salt by dissolving and rinsing with water. The resultant highly porous scaffold can then be sterilized and seeded with micro-dissected human dermal papilla or other suitable source of follicle progenitor cells and cultured in vitro until the entire porous structure is populated with cultured cells. This tissue-engineered construct then can be cut up into a large number of fragments, each about the size of a normal human dermal papilla. These irregular shaped fragments can be suspended in culture media and cultured further until the desired smooth surfaced structure is obtained. These tissue engineered dermal papilla can be implanted or injected into the skin to initiate the process of follicle neogenesis for hair restoration.

Alternatively, the porous scaffolds of the present invention can also be made according to the following method (hereinafter, the "pressed mold method"), comprising the following steps:

1. Provide a thin, non-woven web of bioabsorbable fibers.
2. Place said web in a two-part mold that has cavities in one part and mating forms in the other part, said cavities and forms providing the desired shape and dimensions of the desired scaffolds.
3. Close the mold and apply sufficient heat and pressure to form the web into the desired porous structure.
4. Remove the web from the mold and die-cut the molded scaffolds from the web.

The non-woven web preferably comprises either fibers that have a core/sheath structure in which the core of the fiber has a higher melting temperature than the sheath, or fibers without such a structure. The fibers in the non-woven web are preferably felted, sintered, or bonded with the use of a solvent or a second polymer dissolved in a solvent.

FIGS. 3–6 illustrate application of the mold method to produce scaffolds of the present invention. FIG. 3 shows a drawing of a non-woven web 12 of bioabsorbable fibers. FIG. 4 shows a two-part mold, comprising a top plate 14 and a bottom plate 17. The top plate features a bottom surface 15 with an array of forms 16 protruding therefrom. The bottom plate features a top surface 18 with depressions 19 therein to receive said forms. FIG. 5 is a slightly raised, angled view of the non-woven web 12' after it has been compressed and heated in the mold of FIG. 4, thereby creating depressions 20 that are molded into the desired shape for scaffolds for tissue engineered hair. FIG. 6 shows molded scaffolds 8' after they have been cut from the depressions 20 in the non-woven web 12' in FIG. 5 by means of a die cutter, and transferred to wells 22 of culture dish 23. The wells 22 are designed to receive scaffolds 8 or 8', culture medium, and cells.

The mold production process described immediately above is particularly well suited for scale-up and mass production. For example, the two-part mold shown in FIG. 4 could be produced in the form of two cylinders rather than two flat plates. The web, in the form of a continuous ribbon, could be embossed with the desired pattern as it is compressed and heated during passage between the two counter-rotating rolls. Die cutters also could be mounded in a rotating cylinder to cut out the scaffolds or the cutter could be an added feature of the embossing rolls. This automated assembly line process would continue with the scaffolds being deposited into cell culture wells that are pre-formed in polyester film. The scaffold-loaded film could be cut and packaged into trays, placed in additional packaging and sterilized.

Other methods of creating porous scaffolds from bioabsorbable materials also can be used in practice of the present invention. Methods such as emulsion freeze-drying, expansion in high pressure gas, 3D printing, and phase separation techniques are discussed in an article by Y. S. Nam and T. G. Park, "Porous biodegradable polymeric scaffolds prepared by thermally induced phase separation", *The Journal of Biomedical Materials Research*, October 1999, vol. 47, no. 1, pages 8–17, the teachings of which are incorporated herein.

A preferred embodiment of the above-mentioned phase separation technique uses poly(d,l-lactide-co-glycolide) (PLGA) as the structural polymer and poly(ethylene glycol) (PEG) as the porogen. Thus a mixture of PLGA and PEG can be dissolved in dichloromethane to give a clear solution, which is then applied to a scaffold form made from a material that is not soluble in dichloromethane, but preferably soluble in water, for example sugar. Upon evaporation of the dichloromethane, the PEG phase separates from the PLGA by crystallization. If the form is made of sugar, then soaking in water dissolves out the PEG as well as the form to leave the resultant desired porous PLGA scaffold.

Scaffolds of the present invention can be used to engineer new hair follicles in a number of ways. In general, the appropriate cells can be seeded on the scaffold and either implanted immediately into the scalp or allowed to multiply in culture on the scaffold prior to implantation. The implantation procedure can be the same technique that hair transplant surgeons currently use to implant single follicles or "mini-grafts". For example, a laser can be used to bore a small hole in the scalp to precisely the desired depth and the cell-seeded scaffold can simply be planted in the hole. As these implanted cells grow they orchestrate the neo-genesis of a new hair follicle. The bioabsorbable scaffold then degrades and is eliminated from the site as the implant matures into a normal, hair-producing follicle.

The cells used to seed the scaffold can be taken from follicles biopsied from the patient or from organ donor follicles. This later option is known to be feasible due to recent research results. Follicle progenitor cells from a human donor were successfully transplanted into an unrelated human recipient where they initiated the formation of new follicles that grew hair. This finding, entitled "Transgender induction of hair follicles", was reported by A. M. Reynolds, C. Lawrence, P. B. Caerhalmi-Friedman, A. M. Christiano and C. A. B. Jahoda in *Nature*, 402, 33–34, Nov. 4, 1999, the teachings of which are incorporated by reference herein. A distinct advantage of the present invention is the ability to multiply the cells in culture before seeding them on the scaffold implants. This both maximizes the number of scaffolds that can be seeded from each harvested follicle and minimizes the labor of dissecting follicles to obtain the desired progenitor cells.

EXAMPLES

Example 1

Poly(ethylene oxide) (hereinafter, "PEO") 100,000 molecular weight purchased from Aldrich Chemical Co. (Milwaukee, Wis. 53201), was melt extruded into a 1.0 mm diameter filament and cut into 2 cm lengths. One of the PEO filaments was dipped into water, hydrating the surface and making it sticky. This was then dipped into sodium chloride crystals that had been ground into fine particles in an electric coffee bean grinder. Excess salt was shaken off and the coating was allowed to dry. A 10% (w/v) solution of poly(d,l-lactide-co-50%-glycolide) (PLGA) (Resomer RG504, Boehringer Ingelheim, Germany) in acetone (Aldrich Chemical Co.) was dripped onto the salt encrusted PEO filament and the excess solution was allowed to run off. Additional powdered salt was sprinkled onto the surface until it was completely covered. After the acetone evaporated, the coated PEO filament was placed in water until all of the salt and PEO dissolved, leaving a hollow filament of porous PLGA which was removed, flattened, and cut into thin strips with a sharp blade. The strips were rolled between finger and thumb and cut into 2 mm lengths. The hollow filament of porous PLGA produced as described above was used to make a form for a scaffold of the present invention, as follows.

Scaffolds of the present invention were produced as follows. A 0.3 mm diameter concentric hole was made in the end of another PEO filament by pressing a heated needle about 2 mm into the PEO. This caused molten PEO to build up around the sides of the filament. Upon cooling, the needle was removed. The hole was then filled with one of the above rolled strips of porous PLGA. The end of the resulting PEO filament was then coated as described above with salt and PLGA solution. Upon evaporation of the acetone and dissolving all of the salt and PEO in water and drying, the desired porous bioabsorbable polymer scaffold was obtained.

Example 2

Human hair follicles are dissected to obtain the dermal papilla, which are transferred to a culture flask containing culture media. After several weeks in culture, the dermal papilla cells multiply and grow over the surface of the cell culture flask. These cells are detached from the flask by treatment with an enzyme and concentrated by centrifugation. The cells are then transferred, after re-suspension, by pipette into the scaffolds of Example 1 and the cell-seeded scaffolds placed in a culture flask with media for several days to allow the cells to adhere to the surfaces of the scaffolds. Culturing of the cell-seeded scaffolds is then continued in another flask of media with gentle stirring until the scaffolds are fully populated with cells.

Example 3

Scaffolds seeded as described in Example 2 are implanted into the scalp of a human experiencing hair loss. Over time, as new hair follicles are created, new hairs grow from the implants, and the scaffolds bioabsorb.

The invention claimed is:
1. A porous scaffold comprising a bioabsorbable polymer and hair follicle progenitor cells;
   wherein the scaffold is about the shape of a hair follicle;

wherein the porous scaffold comprises a fibrous structure; and wherein the fibrous structure comprises fibers that are bonded together.

2. The scaffold of claim 1, in which the fibers comprise a core and a sheath, the sheath having a lower melting point than melting point of the core, and the fibers are bonded together by inter-fiber welds at at least one point of contact between the fibers.

3. A method of making a porous scaffold comprising a bioabsorbable polymer and hair follicle progenitor cells, wherein the scaffold is about the shape of a hair follicle, comprising the steps of:
   a. providing a bioabsorbable polymer soluble in a first solvent;
   b. providing a form comprising a hair follicle shaped region and comprising a material soluble in a second solvent and substantially insoluble in the first solvent;
   c. coating the form with particles of a pore-forming substance soluble in the second solvent or in a third solvent;
   d. dissolving the bioabsorbable polymer in the first solvent and applying the dissolved polymer to the coated form;
   e. removing the first solvent;
   f. dissolving the form and the particles in the second solvent;
   g. removing the second solvent to form a scaffold; and
   h. seeding the scaffold with hair follicle progenitor cells.

4. The method of claim 3, further comprising using the third solvent to remove the particles.

5. A method of making a porous scaffold comprising a bioabsorbable polymer and hair follicle progenitor cells, wherein the scaffold is about the shape of a hair follicle, comprising the steps of:
   a. providing a bioabsorbable polymer soluble in a first solvent and substantially insoluble in a second solvent;
   b. providing a form comprising a hair follicle shaped region and comprising a material soluble in the second solvent and substantially insoluble in the first solvent;
   c. providing a pore-forming substance soluble in both the first and the second solvents;
   d. coating the form with a solution comprising the bioabsorbable polymer and the pore-forming substance dissolved in the first solvent;
   e. removing the first solvent and causing the pore-forming substance to phase separate from the bioabsorbable polymer;
   f. dissolving the form and the pore-forming substance with the second solvent;
   g. removing the second solvent to produce a porous scaffold; and
   h. seeding the scaffold with hair follicle progenitor cells.

6. The method of claim 5, in which the bioabsorbable polymer comprises a copolymer of d,l-lactide and glycolide, the pore-forming substance comprises poly(ethylene glycol), the form comprises sugar, the first solvent comprises dichloromethane and the second solvent comprises water.

7. A method of making a porous scaffold comprising a bioabsorbable polymer and hair follicle progenitor cells, wherein the scaffold is about the shape of a hair follicle, comprising the steps of:
   a. providing a thin, non-woven web of bioabsorbable fibers;
   b. placing the web in a two-part mold comprising a first part having cavities and a second part having mating forms, the cavities and mating forms together providing a hair follicle shaped region;
   c. closing the mold and applying sufficient heat and pressure to form the web into a porous structure; and
   d. removing the web from the mold;
   e. die-cutting the scaffold from the web;
   f. seeding the scaffold with hair follicle progenitor cells.

8. A method of implanting hair follicle progenitor cells comprising implanting a porous scaffold comprising a bioabsorbable polymer and hair follicle progenitor cells into skin where growth of new hair is desired, wherein the scaffold is about the shape of a hair follicle.

9. The method of claim 8, in which the progenitor cells are obtained from a substructure within a normal hair follicle.

10. The method of claim 9, in which the progenitor cells are cultured prior to seeding the cells on the scaffold.

11. The method of claim 9, wherein the substructure is selected from the group consisting of dermal papilla, dermal sheath and bulge area.

12. The method of claim 8, in which the method of implantation of the scaffold is substantially equivalent to procedures used by hair transplant surgeons to implant single hair grafts into the skin.

* * * * *